US010342836B2

(12) United States Patent
Kim et al.

(10) Patent No.: US 10,342,836 B2
(45) Date of Patent: Jul. 9, 2019

(54) COMPOSITION HAVING A FUNCTION FOR ALLEVIATING PREMENSTRUAL SYNDROME AND MENSTRUAL PAIN

(71) Applicant: AMOREPACIFIC CORPORATION, Seoul (KR)

(72) Inventors: Su Hwan Kim, Yongin-si (KR); Chan Woong Park, Yongin-si (KR); Jeong Hwa Jang, Yongin-si (KR); Wan Gi Kim, Yongin-si (KR); Sang Jun Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 558 days.

(21) Appl. No.: 14/902,392

(22) PCT Filed: Jun. 19, 2014

(86) PCT No.: PCT/KR2014/005392
§ 371 (c)(1),
(2) Date: Dec. 31, 2015

(87) PCT Pub. No.: WO2015/002391
PCT Pub. Date: Jan. 8, 2015

(65) Prior Publication Data
US 2016/0367614 A1 Dec. 22, 2016

(30) Foreign Application Priority Data

Jul. 4, 2013 (KR) .................. 10-2013-0078238
Apr. 30, 2014 (KR) .................. 10-2014-0052770

(51) Int. Cl.
| A61K 36/00 | (2006.01) |
| A61K 36/258 | (2006.01) |
| A61K 31/07 | (2006.01) |
| A61K 31/122 | (2006.01) |
| A61K 31/197 | (2006.01) |
| A61K 31/375 | (2006.01) |
| A61K 31/4415 | (2006.01) |
| A61K 31/455 | (2006.01) |
| A61K 31/51 | (2006.01) |
| A61K 31/525 | (2006.01) |
| A61K 31/704 | (2006.01) |
| A61K 33/06 | (2006.01) |
| A61K 33/26 | (2006.01) |
| A61K 33/30 | (2006.01) |
| A23L 33/105 | (2016.01) |
| A61K 31/355 | (2006.01) |
| A61K 31/519 | (2006.01) |
| A61K 33/00 | (2006.01) |
| A61K 33/42 | (2006.01) |

(52) U.S. Cl.
CPC .......... *A61K 36/258* (2013.01); *A23L 33/105* (2016.08); *A61K 31/07* (2013.01); *A61K 31/122* (2013.01); *A61K 31/197* (2013.01);

*A61K 31/355* (2013.01); *A61K 31/375* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/704* (2013.01); *A61K 33/00* (2013.01); *A61K 33/06* (2013.01); *A61K 33/26* (2013.01); *A61K 33/30* (2013.01); *A61K 33/42* (2013.01); *A23V 2002/00* (2013.01)

(58) Field of Classification Search
CPC .................................................... A61K 36/00
USPC ........................................................ 424/725
See application file for complete search history.

(56) References Cited

U.S. PATENT DOCUMENTS

| 2002/0136785 A1 | 9/2002 | Yuan |
| 2004/0101934 A1 | 5/2004 | Choe et al. |
| 2006/0127379 A1 | 6/2006 | Kim et al. |
| 2010/0297270 A1 | 11/2010 | Park et al. |

FOREIGN PATENT DOCUMENTS

| CN | 1640436 A | | 7/2005 |
| CN | 2008186394 | * | 3/2008 |
| CN | 101720225 A | | 6/2010 |
| EP | 2368559 | | 9/2011 |
| EP | 2982377 | | 2/2016 |
| JP | 2010528108 A | | 8/2010 |
| KR | 1020080104600 A | | 12/2008 |
| KR | 1020110089036 A | | 8/2011 |
| KR | 1020110104259 A | | 9/2011 |
| KR | 1020120005195 A | | 1/2012 |
| KR | 1020130033591 A | | 4/2013 |

OTHER PUBLICATIONS

Japanese Office Action with English Translation for Application No. 2016-523631 dated Jan. 9, 2018.
Lee, et al., Chemical constituents and biological activities of the berry of Panax ginseng, Journal of Medicinal Plants Research vol. 4(5), pp. 349-353, Mar. 4, 2010.
International Search Report with English Translation for International Application No. PCT/KR2014/005392 dated Sep. 22, 2014.
Written Opinion for International Application No. PCT/KR2014/005392 dated Sep. 22, 2014.
Supplemental European Search Report—European patent application No. 14819802.1 dated Feb. 15, 2017.
Jin Xudan, "Fantastic Elements", Inner Mongolia Publishing House, Jan. 1, 2017, 1st edition, p. 113.

(Continued)

Primary Examiner — Michael V Meller
(74) Attorney, Agent, or Firm — Cantor Colburn LLP

(57) ABSTRACT

The present disclosure relates to a composition containing *ginseng* fruit extract. The present disclosure also relates to a composition for relieving premenstrual syndrome and menstrual pain, which contains *ginseng* fruit extract. The composition according to the present disclosure exhibits an effect of relieving or improving the symptoms of premenstrual syndrome and thus can be used as a pharmaceutical composition or a food composition.

10 Claims, 2 Drawing Sheets

(56) References Cited

OTHER PUBLICATIONS

"Protective effect and mechanism of ginseng saponin RE on myocardial ischemia-reperfusion injury in rats", China Excellent Master's Thesis Full-text Database Medical and Health Sciences, Oct. 16, 2008, No. 11, E057-200.

Chinese Office Action dated Jan. 30, 2019 of Chinese Application No. 201480038214.6.

Peng Mingquan, "Pillage Method", Chengdu Times Publishing House, Mar. 1, 2003, 1st edition, p. 146.

\* cited by examiner

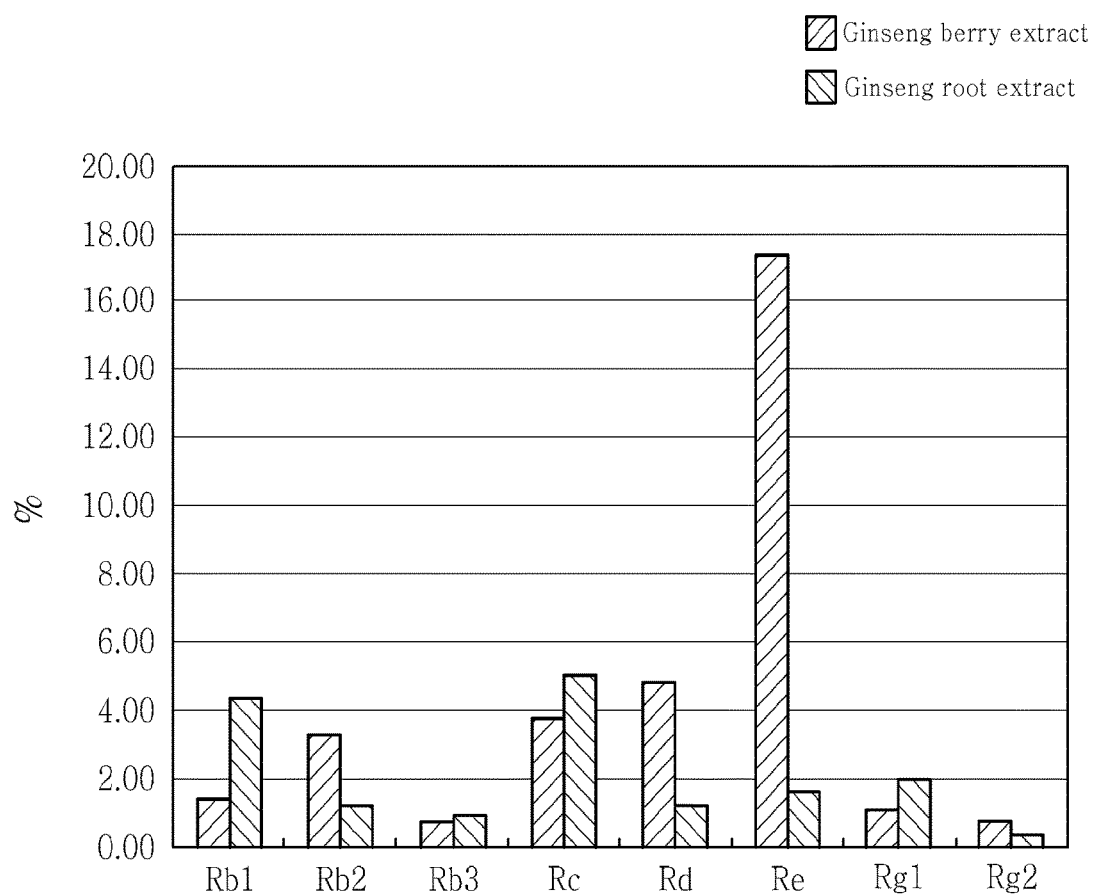
[Fig. 1]

[Fig. 2]

COMPOSITION HAVING A FUNCTION FOR ALLEVIATING PREMENSTRUAL SYNDROME AND MENSTRUAL PAIN

TECHNICAL FIELD

The present disclosure relates to a composition containing *ginseng* fruit extract.

BACKGROUND ART

*Ginseng* (*Panax ginseng* C. A. Meyer) is a plant belonging to the genus *Panax* of the family Araliaceae. It has been empirically used as herbal medicine from 2,000 years ago in Korea, China, Japan, etc. to prevent diseases and extending life. The effects and efficacies of *ginseng* known thus far include action on the central nervous system, anticarcinogenic action, anticancer action, immunomodulatory action, antidiabetic action, liver function improving effect, action of improving cardiovascular disorders, anti antiatherosclerotic action, blood pressure controlling action, action of improving menopausal disorder, effect on osteoporosis, anti-stress action, anti-fatigue action, antioxidant action, antiaging effect, etc. (The Recent Korean *Ginseng*: Constituents and Effects, Korea *Ginseng* and Tobacco Research Institute, 56-112, 1996).

Ginsenosides, which are the representative physiologically active ingredients of *ginseng*, are distributed uniformly in the areal and subterranean parts of *ginseng*. However, it is known that the contents and compositions of ginsenosides differ depending on the parts such as root, leaf, fruit, etc. (Attele A S et al, *Biochem Pharmacol*, 58; 1685-1693, 1999).

Premenstrual syndrome (PMS) refers to emotional and physical symptoms related to a woman's menstrual cycle, occurring in women of child-bearing age during the menstrual cycle following ovulation (American Psychiatric A, American Psychiatric Association Washington D.C., 1994, ACGO Practice B. *Obstetrics and Gynecology* 95(1), 1-9, 2000). 80% of women suffer from mild physical and mental symptoms of PMS (Hylan T R et al, *Journal of Women's Health and Gender Based Medicine* 8(8), 1043-1052, 1999). And, 24-32% of women of child-bearing age suffer from moderate or severe symptoms (Campell E M et al, *Journal of Reproductive Medicine* 42(10) 637-646, 1997). The symptoms cause great social and economic losses owing to limited women's activities.

Common physical, behavioral and emotional symptoms are as follows (Freeman E W, *Psychoneuroendocrinology* 28, 25-37, 2003).

| Physical | Behavioral | Mood |
| --- | --- | --- |
| Swelling | Sleep disturbances | Irritability |
| Breast tenderness | Appetite changes | Mood swings |
| Aches | Poor concentration | Anxiety/tension |
| Headache | Decreased interest | Depression |
| Bloating/weight gain | Social withdrawal | Feeling out of control |

At present, little is known about the specific ingredients included in *ginseng* fruit and their functions related to relieving of premenstrual syndrome and menstrual pain.

DISCLOSURE

Technical Problem

The present disclosure is directed to providing a composition containing *ginseng* fruit, which provides a novel use for human health, i.e. relieving premenstrual syndrome and menstrual pain.

Technical Solution

In a general aspect, the present disclosure provides a composition for relieving premenstrual syndrome and menstrual pain, containing *ginseng* fruit extract as an active ingredient.

In another general aspect, the present disclosure provides a composition for relieving and improving premenstrual syndrome, containing *ginseng* fruit extract as an active ingredient.

Advantageous Effects

A composition according to the present disclosure, which contains *ginseng* fruit extract, may effectively relieve and improve premenstrual syndrome and menstrual pain.

Accordingly, the composition according to the present disclosure can be widely used in the field of food and medicine.

BRIEF DESCRIPTION OF DRAWINGS

FIG. 1 shows a result of analyzing the ginsenoside components of *ginseng* fruit extract according to the present disclosure and *ginseng* root extract for comparison.

FIG. 2 shows a result of comparing premenstrual syndrome before and after intake of *ginseng* fruit extract according to the present disclosure.

MODE FOR INVENTION

Korean Patent Application No. 10-2013-0078238, which was filed on Jul. 4, 2013 and Korean Patent Application No. 10-2014-0052770, which was filed on Apr. 30, 2014 are incorporated herein in its entirety for all purposes. In addition, this application claims the priority of Korean Patent Application No. 10-2013-0078238 and Korean Patent Application No. 10-2014-0052770 and all the benefits accruing therefrom, the contents of which in its entirety are herein incorporated by reference.

Hereinafter, the present disclosure is described in detail.

In an aspect, the present disclosure provides a composition for improving or relieving premenstrual syndrome and menstrual pain, as an active ingredient, containing ginsenoside Re or *ginseng* fruit extract containing the Re.

In an exemplary embodiment, the present disclosure may relate to a method for improving or relieving premenstrual syndrome and menstrual pain, including administering ginsenoside Re or *ginseng* fruit extract containing the Re to an individual in need of improvement or relieving of premenstrual syndrome and menstrual pain. Specifically, in an exemplary embodiment of the present disclosure, the administration may follow the administration method or administration dose described in the present disclosure.

In an exemplary embodiment, the present disclosure may relate to a use of ginsenoside Re or *ginseng* fruit extract containing the Re for improving or relieving premenstrual syndrome and menstrual pain.

In an exemplary embodiment, the present disclosure may relate to ginsenoside Re or *ginseng* fruit extract containing the Re for use in improving or relieving premenstrual syndrome and menstrual pain.

In an exemplary embodiment of the present disclosure, the premenstrual syndrome refers to emotional, behavioral and physical symptoms occurring repetitively prior to menstruation. Common symptoms may include physical symptoms such as breast pain, bloating, headache, etc. and psychological symptoms such as mood swings, depression, uneasiness, aggressiveness, etc. These symptoms become gradually severe following ovulation, reaching the culmination a week before menstruation, and disappear in a few days once the menstruation begins.

In an exemplary embodiment of the present disclosure, the premenstrual syndrome may include emotional symptoms such as poor concentration, aggressiveness, depression, uneasiness, etc. and physical symptoms such as edema, breast pain, digestive disorder, headache, back pain, etc. and the composition according to the present disclosure may be a composition for improving or relieving such symptoms.

The *ginseng* fruit used in the present disclosure exhibits difference in components and composition from the commonly used *ginseng* root.

In the present disclosure, the *ginseng* fruit may contain more mineral components including vitamins as compared to the *ginseng* root. Also, the *ginseng* fruit contains more ginsenosides than the *ginseng* root and the composition of the ginsenosides is also different.

In an exemplary embodiment, since the *ginseng* fruit extract may contain more protopanaxatriol (PT) ginsenosides such as ginsenosides Re, Rg1, Rg2, etc. than protopanaxadiol (PD) ginsenosides such as ginsenosides Rb1, Rb2, Rc, Rd, etc., the present disclosure may provide a different effect. For example, it is reported that *ginseng* fruit exhibits better antidiabetic effect than *ginseng* root (Dey L. et al., *Phytomedicine*, 10; 600-605, 2003).

In the present disclosure, the ginsenosides may be obtained from *ginseng* fruit.

The exact causes of premenstrual syndrome are not fully understood and explanation can be given based on biological phenomena. Although it is reported that it is not associated with the level of a specific hormone, decrease in progesterone, change in estrogen level and change in the estrogen/progesterone ratio are thought of as possible causes (Kim T H, *Journal of Soonchunhyang Medical Science* 14(3), 79-84, 2009). In general, it is thought that PMS and menstrual pain are caused by a combination of the above-described factors as well as environmental factors.

The chemical structure of ginsenoside Re which is present in *ginseng* fruit extract in large quantity is shown in Chemical Formula 1.

[Chemical Formula 1]

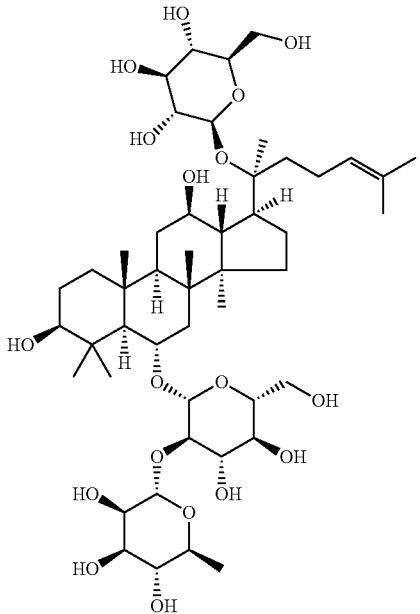

In an exemplary embodiment of the present disclosure, ginsenoside Re may be contained in an amount of 5-30 wt % or 10-25 wt % based on the total weight of the *ginseng* fruit extract. Specifically, in an exemplary embodiment of the present disclosure, ginsenoside Re may be contained in the *ginseng* fruit extract in an amount of 0.1 wt % or greater, 1 wt % or greater, 5 wt % or greater, 7 wt % or greater, 10 wt % or greater, 12.5 wt % or greater, 13 wt % or greater, 15 wt % or greater, 17 wt % or greater, 20 wt % or greater, 23 wt % or greater, 25 wt % or greater, 27 wt % or greater, 30 wt % or greater, 35 wt % or greater or 40 wt % or greater and 45 wt % or less, 40 wt % or less, 35 wt % or less, 30 wt % or less, 25 wt % or less, 23 wt % or less, 20 wt % or less, 17 wt % or less, 15 wt % or less, 13 wt % or less, 12.5 wt % or less, 10 wt % or less, 7 wt % or less, 5 wt % or less or 1 wt % or less, based on the total weight of the *ginseng* fruit extract.

In an exemplary embodiment of the present disclosure, the *ginseng* fruit extract may have a protopanaxadiol (PD) ginsenoside to protopanaxatriol (PT) ginsenoside weight ratio (PD/PT) of 0.1-1.5 or 0.4-0.9. Specifically, in an exemplary embodiment of the present disclosure, the protopanaxadiol (PD) ginsenoside to protopanaxatriol (PT) ginsenoside weight ratio (PD/PT) may be 0.1 or greater, 0.15 or greater, 0.2 or greater, 0.25 or greater, 0.3 or greater, 0.35 or greater, 0.4 or greater, 0.45 or greater, 0.5 or greater, 0.55 or greater, 0.6 or greater, 0.65 or greater, 0.69 or greater, 0.7 or greater, 0.73 or greater, 0.75 or greater, 0.8 or greater, 0.85 or greater, 0.9 or greater, 0.95 or greater or 1.0 or greater and 1.5 or smaller, 1.3 or smaller, 1.0 or smaller, 0.95 or smaller, 0.9 or smaller, 0.85 or smaller, 0.8 or smaller, 0.75 or smaller, 0.73 or smaller, 0.7 or smaller, 0.69 or smaller, 0.65 or smaller, 0.6 or smaller, 0.55 or smaller, 0.5 or smaller, 0.45 or smaller, 0.4 or smaller, 0.3 or smaller, 0.2 or smaller or 0.1 or smaller. Specifically, in an exemplary embodiment of the present disclosure, the protopanaxadiol (PD) ginsenoside to protopanaxatriol (PT) ginsenoside weight ratio (PD/PT) may be 0.69 or 0.73.

Since the *ginseng* fruit extract may contain vitamins, minerals, ginsenosides, anthocyanins, etc. in large quantities, a composition according to an exemplary embodiment of the present disclosure may improve and relieve the symptoms of premenstrual syndrome (PMS) and menstrual pain.

In an exemplary embodiment of the present disclosure, the *ginseng* fruit extract may be prepared by a method comprising:

(a) pretreating *ginseng* fruit; and (b) extracting the pretreated *ginseng* fruit with water or an organic solvent.

In the step (a), the *ginseng* fruit may be live *ginseng* fruit and the pulp and rind of the *ginseng* fruit may be dried under sunlight or hot air.

Specifically, in an exemplary embodiment of the present disclosure, the pretreatment may be drying the *ginseng* fruit and the drying method may be one commonly employed by those skilled in the art to dry plant fruit such as *ginseng* fruit, without particular limitation. Specifically, in an exemplary embodiment of the present disclosure, the drying may be sun drying, hot air drying, evaporation drying, spray drying or freeze drying, more specifically sun drying or hot air drying. More specifically, in an exemplary embodiment of the present disclosure, the pretreatment may include: isolating and removing seeds from the *ginseng* fruit; and drying the pulp and rind of the *ginseng* fruit.

In an exemplary embodiment of the present disclosure, the method may further include, after the step (b), (c) concentrating the resulting extract.

Further, in the step (b), the *ginseng* fruit extract may be prepared by extracting dried *ginseng* fruit at room temperature using water or an organic solvent under reflux, followed by concentration under reduced pressure. The organic solvent may be ethanol.

In an exemplary embodiment of the present disclosure, the concentration may be concentration under reduced pressure but any method well known by those skilled in the art may be employed without particular limitation. Specifically, in an exemplary embodiment of the present disclosure, the concentration may be concentration under reduced pressure and the concentration under reduced pressure may be performed at 40-45° C.

In an exemplary embodiment of the present disclosure, the method may further include, after the step (c), (d) removing oil-soluble components.

In an exemplary embodiment of the present disclosure, the oil-soluble components may be removed using a separatory funnel by dissolving the *ginseng* fruit extract in water and then adding diethyl ether.

In an exemplary embodiment of the present disclosure, the method may further include, after the step (d), (e) extracting the extract with the oil-soluble components removed by adding an organic solvent.

Specifically, in an exemplary embodiment of the present disclosure, the step (e) may include, after extracting the extract by adding the organic solvent, concentrating the extract to obtain a *ginseng* fruit extract.

In an exemplary embodiment of the present disclosure, the *ginseng* fruit extract may be prepared by, for example: removing seeds from live *ginseng* fruit and drying the pulp and rind of the *ginseng* fruit by hot air drying; and extracting 500 g to 1.5 kg of the dried *ginseng* fruit at room temperature under reflux by adding 2-4 L of water or ethanol, filtering the resulting extract and then concentrating the same at 40-45° C. under reduced pressure, although not being limited thereto. In the present disclosure, the extraction may be performed by, for example, hot water extraction, heat extraction, cold water extraction, reflux extraction, reflux cooling extraction, ultrasonic extraction, etc. Any extraction method commonly employed by those skilled in the art may be used without limitation. Although the extraction may be performed at room temperature, for more effective extraction, it may be performed under heating condition, specifically at about 40-100° C., more specifically at about 80° C., although not being limited thereto. Extraction time may be specifically about 2-4 hours, more specifically about 3 hours, although not being limited thereto. The extraction time may vary depending on conditions such as extraction solvent, extraction temperature, etc. Specifically, the extraction may be performed at 90-100° C. when water is used as the solvent and at 65-70° C. when ethanol is used as the solvent. The extraction may be repeated more than once to obtain the active ingredients in higher yield, specifically 1-5 times, more specifically 3 times. Specifically, in an exemplary embodiment of the present disclosure, reflux extraction may be performed at room temperature.

In an exemplary embodiment of the present disclosure, the mineral may be one or more of at least 4000 mg/100 g of potassium, at least 600 mg/100 g of calcium, at least 40 mg/100 g of iron, at least 150 mg/100 g of phosphorus, at least 250 mg/100 g of magnesium and at least 140 mg/100 g of zinc based on the total weight of the extract.

In an exemplary embodiment of the present disclosure, the mineral may include 4000 mg/100 g to 10 g/100 g of potassium, 600 mg/100 g to 5 g/100 g of calcium, 40 mg/100 g to 1 g/100 g of iron, 150 mg/100 g to 1 g/100 g of phosphorus, 250 mg/100 g to 5 g/100 g of magnesium and 140 mg/100 g to 5 g/100 g of zinc, although not being limited thereto.

In an exemplary embodiment of the present disclosure, the vitamin may be one or more of at least 150 µg/100 g of vitamin A, at least 8 mg/100 g of vitamin $B_1$, at least 5 mg/100 g of vitamin $B_2$, at least 8 mg/100 g of vitamin $B_6$, at least 3 mg/100 g of vitamin C, at least 180 µg/100 g of vitamin K, at least 3.5 mg/100 g of niacin, at least 4 mg/100 g of pantothenic acid and at least 250 µg/100 g of folic acid based on the total weight of the extract.

In an exemplary embodiment of the present disclosure, the vitamin may include 150 µg/100 g to 20 mg/100 g of vitamin A, 8 mg/100 g to 5 g/100 g of vitamin $B_1$, 5 mg/100 g to 5 g/100 g of vitamin $B_2$, 8 mg/100 g to 5 g/100 g of vitamin $B_6$, 3 mg/100 g to 5 g/100 g of vitamin C, 180 µg/100 g to 20 mg/100 g of vitamin K, 3.5 mg/100 g to 5 g/100 g of niacin, 4 mg/100 g to 5 g/100 g of pantothenic acid and 250 µg/100 g to 20 mg/100 g of folic acid, although not being limited thereto.

In an exemplary embodiment of the present disclosure, the composition may contain at least 20 ppm, specifically 20-1000 ppm, of the anthocyanin based on the total weight of the extract, although not being limited thereto.

The composition according to an exemplary embodiment of the present disclosure may contain 0.01-100 wt % of ginsenoside Re or *ginseng* fruit extract containing the Re depending on the type of the composition. Specifically, in an exemplary embodiment of the present disclosure, the ginsenoside Re or the *ginseng* fruit extract containing the same may be contained in an amount of 0.01 wt % or more, 0.1 wt % or more, 1 wt % or more, 5 wt % or more, 10 wt % or more, 20 wt % or more, 30 wt % or more, 40 wt % or more, 50 wt % or more, 60 wt % or more, 70 wt % or more, 80 wt % or more, 90 wt % or more or 99 wt % or more and 100 wt % or less, based on the total weight of the composition.

In an exemplary embodiment of the present disclosure, the *ginseng* fruit extract may contain at least 20 wt % of crude saponin based on the total weight of the *ginseng* fruit extract. Specifically, in an exemplary embodiment of the present disclosure, the *ginseng* fruit extract may contain 20 wt % or more, 22 wt % or more, 24 wt % or more, 26 wt % or more, 28 wt % or more, 30 wt % or more, 31 wt % or more, 32 wt % or more, 33 wt % or more, 35 wt % or more, 37 wt % or more, 40 wt % or more or 45 wt % or more and 50 wt % or less, 46 wt % or less, 44 wt % or less, 42 wt % or less, 40 wt % or less, 38 wt % or less, 36 wt % or less, 34 wt % or less, 32 wt % or less, 30 wt % or less, 28 wt % or less, 26 wt % or less or 24 wt % or less of crude saponin based on the total weight of the *ginseng* fruit extract.

In an exemplary embodiment of the present disclosure, the *ginseng* fruit extract may be a water or $C_1$-$C_6$ lower alcohol extract. Specifically, in an exemplary embodiment of the present disclosure, the $C_1$-$C_6$ lower alcohol may be one or more selected from a group consisting of methanol, ethanol, propanol, butanol, and hexanol, but is not limited thereto.

In an exemplary embodiment of the present disclosure, the *ginseng* fruit extract may be crude saponin extract of *ginseng* fruit. Specifically, in an exemplary embodiment of the present disclosure, the crude saponin extract of *ginseng* fruit may be one obtained by removing oil-soluble components from *ginseng* fruit extract and then extracting the same with an organic solvent. Specifically, the organic solvent may be an organic solvent of low polarity such as, e.g., hexane, methylene chloride, ethyl acetate or butanol. Accordingly, in an exemplary embodiment of the present disclosure, the crude saponin extract of *ginseng* fruit may be a water-soluble fraction extracted with the organic solvent of low polarity.

In an exemplary embodiment of the present disclosure, the composition may be in the form of a formulation selected from a group consisting of powder, granule, tablet, soft or hard capsule and drink, but is not limited thereto.

In the present disclosure, the "extract" refers to any substance extracted from a natural product, regardless of extraction method, extraction solvent, extracted components or extract type. Also, it includes a substance that may be obtained by processing or otherwise treating the resulting substance. Specifically, the processing or treatment of the extract may be fermentation or enzymatic treatment. Accordingly, in the present disclosure, the term extract is used in a broad sense, including fermentation product, concentration product and dried product. Specifically, the extract may be a fermentation product.

In the present disclosure, the "*ginseng* fruit extract" refers to any substance extracted from *ginseng* fruit, regardless of extraction method, extraction solvent, extracted components or extract type. It includes a substance obtained by treating the substance with heat, acid, base, enzyme, etc. Also, it includes a substance that may be obtained by processing or otherwise treating the extracted components of *ginseng* fruit. Specifically, the processing or treatment of the *ginseng* fruit extract may be fermentation or enzymatic treatment. Accordingly, in the present disclosure, the *ginseng* fruit extract may be a fermentation product of *ginseng* fruit extract. Also, the *ginseng* fruit extract may be an extract of live *ginseng* fruit or dried *ginseng* fruit. In the present disclosure, the live *ginseng* fruit, dried *ginseng* fruit or processed *ginseng* fruit (e.g., fermentation product, dried powder, etc.) that may be used for the extraction may be similar or identical in composition. Accordingly, the live *ginseng* fruit, dried *ginseng* fruit or other processing products of *ginseng* fruit having similar or identical composition may provide the same effect and use of the *ginseng* fruit extract described in the present disclosure.

In an exemplary embodiment of the present disclosure, the "*ginseng* fruit" may be in the form of extract, live *ginseng* fruit, pulverized *ginseng* fruit, dried *ginseng* fruit, dried powder of *ginseng* fruit or fermentation product of *ginseng* fruit, although not being limited thereto. The present disclosure is not limited in how to obtain the *ginseng* fruit. It may be cultivated or purchased commercially. In the present disclosure, the *ginseng* fruit needs not necessarily be dried and may be in any form as long as it is suitable to extract the active ingredients of *ginseng* fruit. In the present disclosure, the live *ginseng* fruit may refer to *ginseng* fruit which has not been dried or processed otherwise after being harvested.

In an exemplary embodiment of the present disclosure, the *ginseng* fruit extract may be prepared by a method including (1) extracting *ginseng* fruit with water, an organic solvent or a combination thereof.

In an exemplary embodiment of the present disclosure, the method may further include, after the step (1), (2) concentrating the resulting extract.

In an exemplary embodiment of the present disclosure, the method may further include, after the step the step (2), (3) removing oil-soluble components from the concentrated extract.

In an exemplary embodiment of the present disclosure, the step (3) may further include extracting with an organic solvent after the removal of the oil-soluble components.

In an exemplary embodiment of the present disclosure, the method may further include, after the step the step (3), (4) concentrating the product resulting from the step (3). Specifically, the product resulting from the step (3) may be a concentration product with the oil-soluble components removed or an extract extracted with an organic solvent after removal of the oil-soluble components.

In an exemplary embodiment of the present disclosure, the *ginseng* fruit extract may be prepared by a method including:

(i) extracting *ginseng* fruit with water, an organic solvent or a combination thereof; and (ii) removing oil-soluble components from the resulting extract.

In an exemplary embodiment of the present disclosure, the method may further include, after the step (ii), (iii) extracting with an organic solvent.

In an exemplary embodiment of the present disclosure, the method may further include, after the step (iii), (iv) concentrating the extract.

In an exemplary embodiment of the present disclosure, the water may be distilled water or purified water and the organic solvent may be one or more selected from a group consisting of alcohol, e.g. $C_1$-$C_6$ lower alcohol such as methanol, ethanol, or n-butanol, acetone, ether, ethyl acetate, diethyl ether, methyl ethyl ketone, chloroform, hexane and methylene chloride, although not being limited thereto. Specifically, in an exemplary embodiment of the present disclosure, the organic solvent used to extract the *ginseng* fruit may be water, ethanol or a combination thereof, and the organic solvent used to remove the oil-soluble components may be an organic solvent which is less polar than the organic solvent used to extract the *ginseng* fruit, e.g., n-butanol.

In an exemplary embodiment of the present disclosure, the *ginseng* fruit extract may be prepared by extracting *ginseng* fruit at room temperature under reflux using water or an organic solvent and concentrating the resulting extract under reduced pressure. The organic solvent may be ethanol. And, in an exemplary embodiment of the present disclosure, the composition may be prepared into a pharmaceutical composition or food composition in the form of tablet, pill, pellet, capsule, granule, powder, ointment, drink, injection, etc.

In an exemplary embodiment, the present disclosure provides a pharmaceutical composition containing ginsenoside Re or *ginseng* fruit extract as an active ingredient, which is prepared according to a commonly employed method. Specifically, the pharmaceutical composition may be prepared by mixing or diluting the active ingredient with a vehicle or encapsulating in a suitable vehicle. When the vehicle is used as a diluent, it may be a solid, semisolid or liquid substance which acts as a carrier, excipient or medium for the active ingredient. Accordingly, the pharmaceutical composition may be in the form of tablet, pill, powder, sachet, elixir, suspension, emulsion, solution, syrup, aerosol, soft or hard gelatin capsule, sterile injection, sterile powder, etc.

Examples of the suitable vehicle, excipient or diluent may include lactose, dextrose, sucrose, sorbitol, mannitol, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. The pharmaceutical composition may further contain filler, anticoagulant, lubricant, wetting agent, fragrance, emulsifier, preservative, etc. The pharmaceutical composition of the present disclosure may be prepared into a formulation which, after being administered into a mammal, can provide quick, continuous or controlled release of the active ingredient according to a method well known in the art.

The pharmaceutical composition of the present disclosure may be administered through various routes, including oral, transdermal, subcutaneous, intravenous, intraperitoneal, intramuscular, topical and iontophoretic routes. Specifically, it may be administered topically or orally.

For a human subject, a general daily administration dose of the active ingredient is 1 mg to 100 g/kg body weight, specifically 50 mg to 80 g/kg body weight, 100 mg to 60 g/kg body weight, 200 mg to 50 g/kg body weight, 300 mg to 40 g/kg body weight, 500 mg to 35 g/kg body weight or 1 g to 30 g/kg body weight, and the administered may be made once or several times a day. However, it is to be understood that the actual administration dose of the active ingredient is determined considering many related factors, including the disease to be treated, administration route, age, sex and body weight of a patient, severity of the disease, etc. Accordingly, the above-described administration dose does not limit the scope of the present disclosure by any means.

In an exemplary embodiment, the present disclosure provides a food composition containing ginsenoside Re or *ginseng* fruit extract as an active ingredient, which is prepared according to a commonly employed method.

The food composition of the present disclosure is not particularly limited in food type. For example, the composition of the present disclosure may be added to such foods as drink, meat, sausage, bread, biscuit, rice cake, chocolate, candy, snack, confectionery, pizza, instant noodle, other noodles, gum, dairy products including ice cream, soup, beverage, alcoholic beverage, vitamin complex, etc. All types of health food are included.

The food composition according to the present disclosure may be an indulgence food or health food composition. The food composition is not particularly limited in formulation. For example, it may be formulated into tablet, granule, powder, liquid such as drink, caramel, gel, bar, etc. The food composition may be prepared by those skilled in the art without difficulty by mixing the active ingredient with ingredients commonly used in the art depending on purpose of use. When used together with the other ingredients, a synergic effect may be provided.

Determination of the administration dose of the active ingredient in the food composition according to the present disclosure is within the level of those skilled in the art. A daily administration dose may be, for example, 0.1-5000 mg/kg/day, more specifically 50-500 mg/kg/day, but is not limited thereto. The administration dose may vary depending on various factors, including the age and physical condition of a subject, presence of complications, etc.

For example, the food composition according to the present disclosure may be in the form of various foods such as chewing gum, caramel, candy, frozen dessert, confectionery, etc. drinks such as soft drink, mineral water, alcoholic beverage, etc. or health functional foods such as vitamin, mineral, etc.

In addition, the food composition according to the present disclosure may contain various nutrients, vitamins, minerals (electrolytes), synthetic or natural flavors, colorants, extenders (cheese, chocolate, etc.), pectic acid and salts thereof, alginic acid and salts thereof, organic acids, protective colloidal thickeners, pH adjusting agents, stabilizers, preservatives, glycerin, alcohols, carbonating agents used in carbonated drinks, etc. Besides, the functional food composition according to the present disclosure may contain natural fruit juice and pulp used to prepare fruit juice beverages and vegetable beverages. These ingredients may be added alone or in combination. The mixing proportion of these additives is not of great importance. Generally, they may be contained in the present disclosure in an amount of about 0-20 wt % based on 100 wt % of the composition.

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

Also, it will be apparent to those skilled in the art that various changes and modifications can be made within the scope of the appended claims without departing from the scope of the present disclosure.

{Example 1} Preparation of *Ginseng* Fruit Extract

Pretreatment of *Ginseng* Fruit

Live *ginseng* fruit was harvested and seeds were removed therefrom. Dried *ginseng* fruit was prepared by drying the pulp and rind of the *ginseng* fruit by sun drying or hot air drying.

Preparation of *Ginseng* Fruit Extract

After adding 3 L of ethanol to 1 kg of the dried *ginseng* fruit, followed by reflux extraction at room temperature for 4 hours, filtration and concentration at 45° C. under reduced pressure, 300 g of *ginseng* fruit extract was obtained.

{Example 2} Preparation of Live *Ginseng* Fruit Extract

The fruit of live *ginseng* (*Panax ginseng* C. A. Meyer) was harvested and seeds were removed therefrom. Then, the juice, pulp and rind of the *ginseng* fruit were mixed. After adding 3 L of ethanol to 1 kg of the resulting mixture, followed by reflux extraction at room temperature for 4 hours, filtration and concentration at 45° C. under reduced pressure, 30 g of *ginseng* fruit extract was obtained.

{Comparative Example 1} Preparation of *Ginseng* Root Extract

*Ginseng* root extract was prepared in the same manner as in Example 1 except for using *ginseng* root instead of *ginseng* fruit.

{Comparative Example 2} Preparation of Red *Ginseng* Extract

After adding 3 L of ethanol to 1 kg of dried *ginseng* root (4-year-old), followed by reflux extraction at room temperature for 4 hours, filtration and concentration at 45° C. under reduced pressure, 300 g of red *ginseng* fruit extract was obtained.

{Test Example 1} Analysis of Composition of *Ginseng* Fruit Extract

<Analysis of Ginsenoside (*Ginseng* Saponin) Composition of *Ginseng* Fruit and *Ginseng* Root>

The *ginseng* fruit extracts of Example 1 and Example 2 and the *ginseng* root extract of Comparative Example 1 were treated with ether to remove oil-soluble components and crude saponin was extracted therefrom using butanol (BuOH). Then, ginsenoside composition was analyzed by HPLC. The result is shown in FIG. 1 and Table 1.

TABLE 1

|  | Example 1 (*ginseng* fruit extract) | Example 2 (live *ginseng* fruit extract) | Comparative Example 1 (*ginseng* root extract) |
| --- | --- | --- | --- |
| Crude saponin content (dry weight) | 33.42% | 31.08% | 16.70% |
| PD/PT ratio | 0.73 | 0.69 | 3.23 |

As seen from FIG. 1 and Table 1, the *ginseng* fruit extracts prepared in Example 1 and Example 2 contained about 2 times more crude saponin than the *ginseng* root extract prepared in Comparative Example 1.

The ratio of protopanaxadiol (PD) ginsenosides Rb1, Rb2, Rc and Rd to protopanaxatriol (PT) ginsenosides Re, Rg1 and Rg2 was 0.73, 0.69 and 3.23, respectively. That is to say, the ginsenosides contained in the *ginseng* fruit and the *ginseng* root showed opposing compositions and contents. In particular, the *ginseng* fruit extract contained ginsenoside Re about 9 times more as compared to the *ginseng* root extract.

<Analysis of Mineral Composition of *Ginseng* Fruit Extract>

For characterization of the *ginseng* fruit extracts prepared in Example 1 and Example 2 as "fruit" different from *ginseng* root, the composition of mineral ingredients including vitamins was analyzed. The result is shown in Table 2.

As seen from Table 2, the *ginseng* fruit according to the present disclosure was very rich in the 16 kinds of minerals including vitamins unlike *ginseng* root.

Accordingly, it was confirmed that the *ginseng* fruit according to the present disclosure contains more *ginseng* saponins and have the opposite saponin composition when compared to *ginseng* root. Also, it was confirmed that the *ginseng* fruit is rich in 16 kinds of minerals including vitamins unlike *ginseng* root. In addition, the extract obtained from *ginseng* fruit and the extract obtained from live *ginseng* fruit had almost identical composition. Therefore, it is considered that the two extracts having similar composition will provide the same effect, as demonstrated in the following test examples.

<Analysis of Anthocyanin Composition of *Ginseng* Fruit Extract>

The anthocyanin components contained in the *ginseng* fruit extract prepared in Example 1 were quantitatively analyzed.

The anthocyanins of *ginseng* fruit were quantitatively analyzed using an anthocyanidin kit (cyanidin chloride, delphinidin chloride, malvidin chloride, pelargonin chloride), a cyanidin derivative kit (cyanidin chloride, cyanine chloride, idein chloride, keracyanin chloride, kuromanin chloride) and standard pelargonidin chloride and petunidin chloride. The result is shown in Table 3.

TABLE 3

| Unit: ppm (μg/g) | *Ginseng* fruit extract of Example 1 |
| --- | --- |
| Malvidin chloride | 12.17 |
| Idein chloride (cyanidin-3-O-galactoside) | 2.36 |
| Pelargonidin chloride | 8.28 |
| Keracyanin chloride | 3.29 |
| Total | 26.1 |

As seen from Table 3, the contents of malvidin chloride, idein chloride, pelargonin chloride and keracyanin chloride were quantitated as 12.17, 2.36, 8.28 and 3.29 ppm, respectively and the sum of the four ingredients was 26.1 ppm. Accordingly, it was confirmed that the *ginseng* fruit is rich in anthocyanins.

{Test Example 2} Evaluation of Improvement in Premenstrual Syndrome and Menstrual Pain The American Psychiatric Association presents the following diagnosis standard for premenstrual syndrome.

According to the standard, women who satisfy at least 5 of the following 11 items and at least one of the first 4 items were selected for test.

TABLE 2

| Ingredients | Ex. 1 | Ex. 2 | Root | Ingredients | Ex. 1 | Ex. 2 | Root |
| --- | --- | --- | --- | --- | --- | --- | --- |
| K (mg/100 g) | 5865.57 | 4977.50 | 1460 | Mg (mg/100 g) | 354.38 | 297.54 | 160 |
| Ca (mg/100 g) | 819.26 | 914.22 | 340 | Zn (mg/100 g) | 178.49 | 201.25 | 1.961 |
| Fe (mg/100 g) | 59.31 | 52.11 | 9.804 | Vit. A (μg/100 g, RE) | 213.11 | 145.85 | — |
| P (mg/100 g) | 187.17 | 156.95 | 340 | Vit. $B_1$ (mg/100 g) | 12.29 | 10.09 | 0.16 |
| Vit. $B_2$ (mg/100 g) | 8.45 | 5.05 | 0.50 | Vit. $B_6$ (mg/100 g) | 10.50 | 15.44 | — |
| Vit. C (mg/100 g) | 4.91 | 7.13 | 6 | Vit. E (mg/100 g, α-TE) | 23.61 | 31.25 | — |
| Vit. K (μg/100 g) | 232.12 | 129.82 | — | Niacin (mg/100 g, NE) | 5.76 | 2.01 | 1.0 |
| Pantothenic acid (mg/100 g) | 5.87 | 6.15 | 0.66 | Folic acid (μg/100 g) | 349.97 | 423.35 | — |

(1) Quick change in emotion; sudden sadness, anger or rage (2) Persistent severe anger and uneasiness (3) Uneasiness and tension (4) Depression and hopelessness (5) Disinterest in daily lives (6) Fatigue or low energy (7) Poor concentration (8) Change in appetite (9) Sleep disturbances

(10) Difficulty in emotion control

(11) Breast tenderness, headache, edema, muscle or joint pain and weight gain

Based on the result of Test Example 1, a composition containing the *ginseng* fruit extract according to the present disclosure was administered to the test group and the change in the symptoms of premenstrual syndrome and menstrual pain before and after the administration was evaluated using questionnaires. For the test, 350 mg tablets containing 100 wt % of the *ginseng* fruit extract of Example 1 and the red *ginseng* extract of Comparative Example 2 were prepared. A table top tablet making machine (Erweka, Germany) was used.

40 women were selected from 48 women of child-bearing ages (in their 20s to 50s) according to the diagnosis standard. They were divided into 4 groups: i.e., unadministered group, red *ginseng* group, ginsenoside Re group, and *ginseng* fruit group. Each group was composed of 10 subjects.

The red *ginseng* group was asked to take the red *ginseng*-containing tablets for 4 weeks, twice a day, two tablets once. That is to say, 1400 mg/day of red *ginseng* extract was administered to them.

The ginsenoside Re group was asked to take tablets containing ginsenoside Re as an active ingredient twice a day, two tablets once. The tablet was prepared such that 240 mg of ginsenoside Re and 1160 mg of dextrin were administered per day (60 mg of ginsenoside Re and 290 mg of dextrin per tablet). The content of ginsenoside Re was determined based on the analysis result shown in FIG. 1 for comparison of the effect of improving premenstrual syndrome and menstrual pain of *ginseng* fruit extract and only ginsenoside Re contained therein.

The *ginseng* fruit group was asked to take the *ginseng* fruit extract-containing tablets for 4 weeks, twice a day, two tablets once. That is to say, 1400 mg/day of *ginseng* fruit extract was administered to them.

The 40 women were asked to answer questionnaires first after menstruation and, after the administration of nothing, the red *ginseng* extract or the *ginseng* fruit extract, to answer questionnaires after the next menstruation was over (about 4 weeks later). The improvement in the symptoms of premenstrual syndrome was evaluated by monitoring the change in total scores based on the questionnaires. One point was given for each item.

The change in total score is shown in Table 4 and the number of the women who felt the symptoms of premenstrual syndrome is given in Table 5. They are also shown in FIG. 2 (N=40).

TABLE 4

|  | Unadministered group (n = 10) | Red ginseng group (n = 10) | Ginsenoside Re group (n = 10) | *Ginseng* fruit group (n = 10) |
| --- | --- | --- | --- | --- |
| Before administration | 78 | 66 | 75 | 70 |
| After administration | 76 | 56 | 66 | 42 |
| Difference | 2 (2.6%) | 10 (15%) | 9 (12%) | 28 (40%) |

TABLE 5

|  | Unadministered group (n = 10) | Red ginseng group (n = 10) | Ginsenoside Re group (n = 10) | *Ginseng* fruit group (n = 10) |
| --- | --- | --- | --- | --- |
| Before administration | 10 | 10 | 10 | 10 |
| After administration | 10 | 8 | 8 | 5 |
| Difference | 0 (0%) | 2 (20%) | 2 (20%) | 5 (50%) |

As seen from Tables 4-5 and FIG. 2, the total score given by the subjects who were administered with the *ginseng* fruit extract was remarkably decreased by 40% unlike those of other groups. Also, the number of subjects who felt the symptoms of premenstrual syndrome was decreased by 50% from 10 to 5 in the *ginseng* fruit group. Accordingly, it was confirmed that the *ginseng* fruit extract is very effective in relieving or improving premenstrual syndrome.

In particular, the *ginseng* fruit extract exhibited much superior effect of relieving or improving premenstrual syndrome and menstrual pain as compared to the red *ginseng* extract or only the ginsenoside Re included in the *ginseng* fruit extract. Therefore, it was confirmed that the *ginseng* fruit extract itself exhibits superior effect of relieving or improving premenstrual syndrome as compared to the ginsenoside Re of similar amount.

Hereinafter, the present disclosure will be described in detail through formulation examples. However, the following formulation examples are for illustrative purposes only and it will be apparent to those of ordinary skill in the art that the scope of the present disclosure is not limited by the formulation examples.

{Formulation Example 1} 100 wt % *Ginseng* Fruit Extract

When preparing the *ginseng* fruit extract of Example 1, it was concentrated to a solid content of 60 wt % or higher and then aged at low temperature to obtain 100 wt % *ginseng* fruit extract in liquid state.

{Formulation Example 2} Soft Capsule 110 mg of *ginseng* fruit extract of Example 1, 0.8 mg of palm oil, 0.48 mg of hydrogenated vegetable oil, 2.4 mg of yellow beeswax and 3.6 mg of lecithin were mixed and filled in a soft capsule according to a commonly employed method.

{Formulation Example 3} Tablet 160 mg of *ginseng* fruit extract of Example 1, 200 mg of glucose and 196 mg of dextrin were mixed, granulated using a fluidized bed dryer and, after adding 7 mg of sugar ester, prepared into a tablet.

{Formulation Example 4} Preparation of Pill 0.9 g of *ginseng* fruit extract of Example 1, 0.3 g of sugar, 1.91 g of starch and 0.56 g of glycerin were mixed and prepared into a pill.

{Formulation Example 5} Granule 160 mg of *ginseng* fruit extract of Example 1, 200 mg of glucose and 196 mg of dextrin were mixed, granulated using a fluidized bed dryer and filled in a pouch.

{Formulation Example 6} Drink 110 mg of *ginseng* fruit extract of Example 1, 10 g of glucose and 2 g of citric acid were mixed and, after adding 188 g of purified water, filled in bottles with 200 mL per bottle. Thus prepared drink was sterilized at 90° C. for 2-3 hours.

{Formulation Example 7} Health Functional Food

A health functional food was prepared according to a commonly employed method with the composition described in Table 6.

TABLE 6

| Ingredients | Contents |
| --- | --- |
| *Ginseng* fruit extract of Example 1 | 100 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

The above contents of the vitamins and minerals are given as specific examples but they may be varied as desired.

{Formulation Example 8} Chewing Gum

Chewing gum was prepared according to a commonly employed method with the composition described in Table 7.

TABLE 7

| Ingredients | Contents |
| --- | --- |
| Gum base | 20 wt % |
| Sugar | 76.36-76.76 wt % |
| *Ginseng* fruit extract of Example 1 | 0.24-0.64 wt % |
| Fruit flavor | 1 wt % |
| Water | 2 wt % |

{Formulation Example 9} Candy

A candy was prepared according to a commonly employed method with the composition described in Table 8.

TABLE 8

| Ingredients | Contents |
| --- | --- |
| Sugar | 50-60 wt % |
| Starch syrup | 39.26-49.66 wt % |
| *Ginseng* fruit extract of Example 1 | 0.24-10.64 wt % |
| Orange flavor | 0.1 wt % |

{Formulation Example 10} Flour-Based Foods 5 wt % of the *ginseng* fruit extract of Example 1 was added to 100 wt % of flour. Bread, cake, cookie, cracker and noodle were prepared using the resulting mixture.

{Formulation Example 11} Dairy Products 5-10 wt % of the *ginseng* fruit extract of Example 1 was added to 100 wt % of milk and various dairy products such as butter and ice cream were prepared using the resulting mixture.

{Formulation Example 12} Grain Powder

Brown rice, barley, glutinous rice and adlay were pregelatinized according to a known method and then dried and pulverized to powder of 60 mesh size. Also, black bean, black sesame and wild sesame were steamed according to a known method and then dried and pulverized to powder of 60 mesh size. The grains and seeds were mixed with the *ginseng* fruit extract of Example 1 as described in Table 9.

TABLE 9

| Ingredients | Contents |
| --- | --- |
| Brown rice | 30 wt % |
| Adlay | 20 wt % |
| Barley | 25 wt % |
| Wild sesame | 7 wt % |
| Black bean | 7 wt % |
| Black sesame | 7 wt % |
| *Ginseng* fruit extract of Example 1 | 3 wt % |
| Gandomera | 0.5 wt % |
| Rehmannia | 0.5 wt % |

{Formulation Example 13} Health Drink

Health drink was prepared according to a commonly employed method with the composition described in Table 10.

TABLE 10

| Ingredients | Contents |
| --- | --- |
| *Ginseng* fruit extract of Example 1 or 2 | 1000 mg |
| Citric acid | 1000 mg |
| Oligosaccharide | 100 g |
| Taurine | 1 g |
| Purified water | balance |

According to a commonly employed method, the above ingredients were mixed and heated for about 1 hour while heating at 85° C. The resulting solution was filtered and sterilized.

The invention claimed is:

1. A method for relieving premenstrual syndrome or menstrual pain in a human in need thereof comprising administering to said human an effective amount of *ginseng* fruit ethanol extract, which comprises ginsenosides, vitamin, a mineral and an anthocyanin, and which relieves premenstrual syndrome or menstrual pain in the human in need thereof.

2. The method according to claim 1, wherein the mineral comprises one or more of at least 4000 mg/100 g of potassium, at least 600 mg/100 g of calcium, at least 40 mg/100 g of iron, at least 150 mg/100 g of phosphorus, at least 250 mg/100 g of magnesium and at least 140 mg/100 g of zinc based on the total weight of the extract.

3. The method according to claim 1, wherein the vitamin comprises one or more of at least 150 μg/100 g of vitamin A, at least 8 mg/100 g of vitamin B1, at least 5 mg/100 g of vitamin B2, at least 8 mg/100 g of vitamin B6, at least 3 mg/100 g of vitamin C, at least 180 μg/100 g of vitamin K, at least 3.5 mg/100 g of niacin, at least 4 mg/100 g of pantothenic acid and at least 250 μg/100 g of folic acid based on the total weight of the extract.

4. The method according to claim 1, wherein the *ginseng* fruit ethanol extract comprises at least 20 ppm of the anthocyanin based on the total weight of the extract.

5. The method according to claim 1, wherein the *ginseng* fruit ethanol extract comprises 5-30 wt % of ginsenosides based on the total weight of the extract.

6. The method according to claim 1, wherein the *ginseng* fruit ethanol extract has a weight ratio of protopanaxadiol ginsenoside to protopanaxatriol ginsenoside of 0.1-1.5.

7. The method according to claim 1, wherein the *ginseng* fruit ethanol extract is present in a composition and the composition comprises 0.01-100 wt % of the *ginseng* fruit ethanol extract, based on the total weight of the composition.

8. The method according to claim 1, wherein the *ginseng* fruit ethanol extract comprises at least 20 wt % of crude saponin, based on the total weight of the *ginseng* fruit extract.

9. The method according to claim 7, wherein the composition is a pharmaceutical composition.

10. The method according to claim 7, wherein the composition is a food composition.

* * * * *